(12) United States Patent
Bolea

(10) Patent No.: US 11,078,035 B2
(45) Date of Patent: Aug. 3, 2021

(54) APPARATUS AND METHOD FOR DISPENSING MICROORGANISM CULTURE PLATES

(71) Applicant: 3M INNOVATIVE PROPERTIES COMPANY, St. Paul, MN (US)

(72) Inventor: Phillip A. Bolea, Grant, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 316 days.

(21) Appl. No.: 15/781,562

(22) PCT Filed: Nov. 22, 2016

(86) PCT No.: PCT/US2016/063237
§ 371 (c)(1),
(2) Date: Jun. 5, 2018

(87) PCT Pub. No.: WO2017/099992
PCT Pub. Date: Jun. 15, 2017

(65) Prior Publication Data
US 2018/0370739 A1   Dec. 27, 2018

Related U.S. Application Data

(60) Provisional application No. 62/263,921, filed on Dec. 7, 2015.

(51) Int. Cl.
| | | |
|---|---|---|
| B65G 59/06 | (2006.01) | |
| C12M 1/00 | (2006.01) | |
| C12M 3/04 | (2006.01) | |
| G01N 35/00 | (2006.01) | |
| B01L 3/00 | (2006.01) | |
| C12M 1/12 | (2006.01) | |
| C12M 1/22 | (2006.01) | |

(52) U.S. Cl.
CPC ......... *B65G 59/066* (2013.01); *B65G 59/067* (2013.01); *C12M 3/043* (2013.01); *C12M 23/04* (2013.01); *C12M 23/10* (2013.01); *C12M 23/22* (2013.01); *C12M 99/02* (2013.01); *B01L 3/505* (2013.01); *B01L 2200/04* (2013.01); *C12M 1/00* (2013.01); *G01N 2035/00039* (2013.01)

(58) Field of Classification Search
None
See application file for complete search history.

(56) References Cited

U.S. PATENT DOCUMENTS

| | | | |
|---|---|---|---|
| 2,385,521 A | 9/1945 | Mean | |
| 3,501,379 A * | 3/1970 | Tate | C12M 99/00 435/286.4 |
| 4,468,914 A * | 9/1984 | Pestes | C12M 23/10 141/102 |
| 4,565,783 A | 1/1986 | Hansen et al. | |

(Continued)

FOREIGN PATENT DOCUMENTS

EP    1 018 544    7/2000

*Primary Examiner* — Holly Kipouros
(74) *Attorney, Agent, or Firm* — Eric E. Silverman

(57) ABSTRACT

An apparatus for dispensing microorganism culture plates, culture plate loader and culture plate reader comprising the same, as well as method dispensing microorganism culture plates, method of loading such culture plates into a culture plate reader, and method of counting microorganism colonies on such culture plates.

17 Claims, 2 Drawing Sheets

(56) References Cited

U.S. PATENT DOCUMENTS

| | | |
|---|---|---|
| 5,089,413 A | 2/1992 | Nelson et al. |
| 5,137,812 A | 8/1992 | Matner |
| 5,232,838 A | 8/1993 | Nelson et al. |
| 5,573,950 A | 11/1996 | Graessle et al. |
| 5,744,322 A | 4/1998 | Krejcarek et al. |
| 5,854,075 A | 12/1998 | Levine et al. |
| 2002/0098116 A1 | 7/2002 | Sugaya et al. |
| 2004/0101951 A1 | 5/2004 | Vent et al. |

\* cited by examiner

APPARATUS AND METHOD FOR DISPENSING MICROORGANISM CULTURE PLATES

CROSS REFERENCE TO RELATED APPLICATIONS

This application is a national stage filing under 35 U.S.C. 371 of PCT/US2016/063237, filed Nov. 22, 2016, which claims the benefit of U.S. Provisional Application No. 62/263,921, filed Dec. 7, 2015, the disclosure of which is incorporated by reference in its entirety herein.

BACKGROUND

Thin film culture plates are described, for example in U.S. Pat. Nos. 4,565,783, 5,089,413, 5,137,812, and 5,232,838, and are commercially available, for example, under the trade designation PETRIFILM plates, which is a registered trademark of 3M Company of St. Paul, Minn., USA or its affiliates in many countries around the world. Thin film culture plates typically include a dry powder containing a gelling substrate and microbial growth nutrients coated onto a surface, for example with an adhesive such as an acrylate adhesive. Typically, the powder is reconstitutable, often by cold water, such that an aqueous sample can be placed in contact with the powder and a cover sheet placed over the sample and substrate. In use, the aqueous sample can hydrate the dry powder to form a gelled medium that can sustain microbial growth. Indicator dyes, which can be adhered to the cover sheet, can then react in the presence of viable microorganisms to give a detectable response that allows visualization of the microorganism colonies that grow on the thin film culture device. Other type of culture plates, such as agar culture plates and petri dishes, are also known.

Microorganisms can be cultured on a variety of types of culture plates, including but not limited to and thin film culture plates such as the culture plates available under the trade designation PETRIFILM plates, from 3M Company of St. Paul, Minn., USA. PETRIFILM plates as well as other culture plates have been used to grow microorganism colonies, which are often counted. While manual counting of colonies is possible, it is also known to use a culture plate reader, such as the PETRIFILM plate reader, commercially available from 3M Company of St. Paul, Minn. USA, for this purpose.

SUMMARY

A culture plate dispensing apparatus can include a base having a first major surface, a front edge, and a back edge as well as a pusher on or above the first major surface of the base. The pusher can be capable of moving from a retracted position to an engaged position; the retracted position is closer to the back edge of the base than the engaged position. The pusher and base can be configured such that when the pusher is in the retracted position the base is capable of supporting one or more culture plates on top of the first major surface of the base. The one or more culture plates can have a back edge positionable near the pusher and a slip cover positionable over the pusher when the pusher is in a retracted position. The culture plate dispensing apparatus can also include an upright member positioned at least in part above a portion of the base near the front edge of the base to form a space between the upright member and the base. The space between the upright member and the base defines a precision gap large enough for a culture plate to pass through. The precision gap can be at least the height of the one or more culture plates and less than twice the height of the one or more culture plate. The pusher in the engaged position is adapted to push one and only one culture plate at least partially through the precision gap.

DETAILED DESCRIPTION

Figure 1:
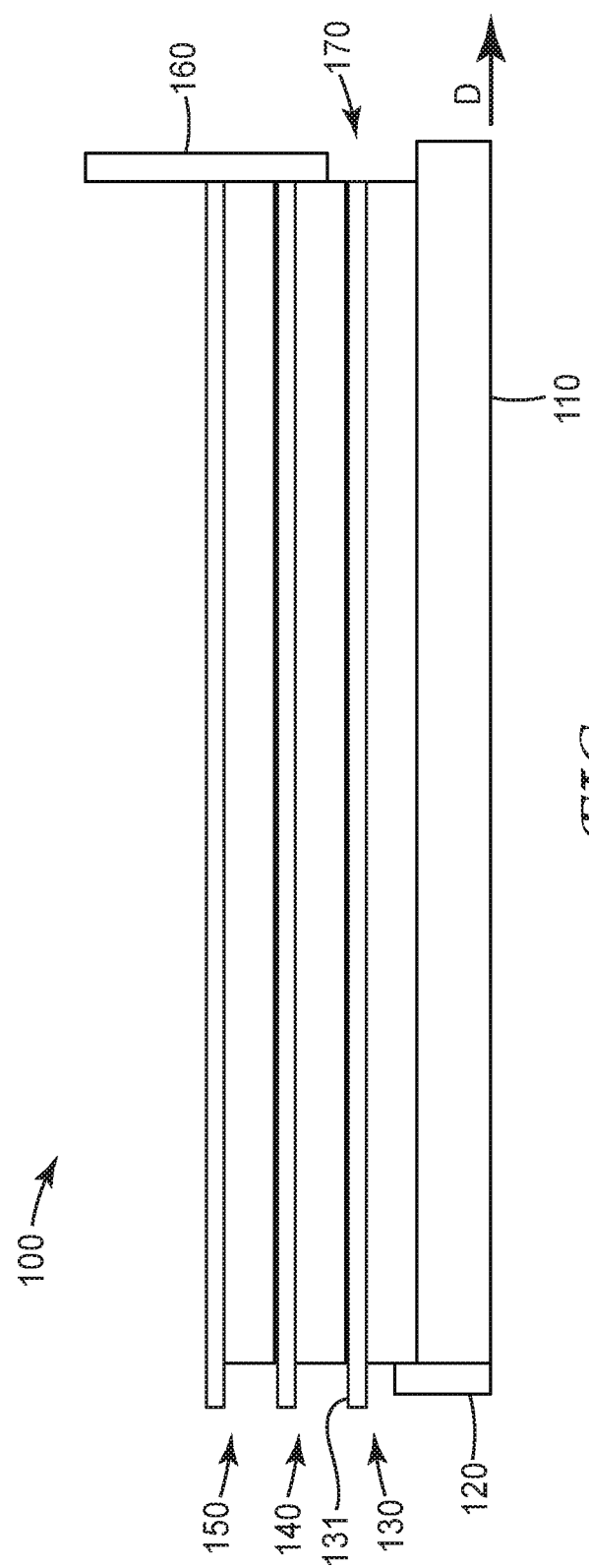
FIG. 1 is a side view of a dispensing apparatus for dispensing a single culture plate from a stack of culture plates.

Throughout this disclosure, singular forms such as "a," "an," and "the" are often used for convenience; however, it should be understood that the singular forms are meant to include the plural unless the singular alone is explicitly specified or is clearly indicated by the context. When the singular alone is called for, a specific term such as "one and only one" is typically used.

Terms of direction such as "upward," "downward," "above," "below," and the like are not necessarily used to indicate direction with respect to the ground or gravity. Instead, such terms are used to indicate relative direction towards or away from particular features. For example, a first feature is "above" a second feature, in some cases such as when the second feature is inverted, be closer to the ground than the second feature; however, two features are "above," "up," "on top," etc. with respect to a common third feature are present in the same relative direction with respect to the common third feature.

"Thin film culture plate," and its plural, refers to a (or for the plural, multiple) culture device(s) that comprises a sheet-like substrate attached to a sheet-like cover slip, the substrate and the cover slip each having an interior-facing major surface and an exterior-facing major surface. Adhered to an interior-facing major surface of the substrate, the cover slip, or both, is a substantially water-free coating that comprises a cold water-soluble gelling agent. Optionally, an interior-facing major surface of the substrate, the cover slip, or both has a substantially water-free coating comprising a nutrient medium adhered thereon. Optionally, the nutrient medium, the gelling agent, or both, may be adhered to an adhesive layer coated on the substrate, the cover slip, or both. Optionally, the thin film culture device may further comprises a thin, apertured spacer adhered to the interior-facing surface of the substrate, the coversheet, or both. Nonlimiting examples of thin film culture devices are disclosed in U.S. Pat. Nos. 4,565,783; 5,089,413; 5,137,812; and 5,232,838.

A culture plate dispensing apparatus can include a base having a first major surface, a front edge, and a back edge as well as a pusher extending on or above the first major surface of the base. The pusher can be capable of moving from a retracted position to an engaged position; the retracted position is closer to the back edge of the base than the engaged position. The pusher and base can be configured such that when the pusher is in the retracted position the base is capable of supporting one or more culture plates on top of the first major surface of the base. The one or more culture plates can have a back edge positionable near the pusher and a slip cover positionable over the pusher when the pusher is in a retracted position. The culture plate dispensing apparatus can also include an upright member positioned at least in part above a portion of the base near the front edge of the base to form a space between the upright member and the base. The space between the upright member and the base defines a precision gap large enough for a culture plate to pass through. The precision gap can be at least the height of the one or more culture plates and less than twice the height of the one or more culture plate. The pusher in the engaged position is adapted to push one and only one culture plate at least partially through the precision gap.

The base of culture plate dispensing apparatus can be specially adapted to support one or more culture plates, and is typically specially adapted to support a stack of multiple culture plates. The base can be in any form suitable for this purpose. In many cases, the base can be a roller or a series of rollers with a belt around them, in which case the outward facing surface of the roller or belt is typically the first major surface of the base. In other cases, the base is a hard flat plate or sheet, such as of plastic or metal, that can have a first major surface that is surface treated or otherwise designed to have low friction between the first major surface and a culture plate resting on top of the first major surface.

The stack of culture plates, which is not part of the apparatus but can reside on the first major surface of the base, can have a stack height that is defined by the number of culture plates and the height of the individual culture plates. Typically, the culture plates will first be inoculated and then dispensed from the dispensing apparatus into a culture plate reader. Some dispensing apparatuses can accommodate 10, 25, 50, 100, 250, 400 or even 500 or more culture plates. The culture plates, which in most cases are thin film culture plates, do not necessarily require a large amount of height. For example, some thin film culture plates available from 3M Company have a height of 1.5 to 2 cm per stack of 50 inoculated thin film culture plates, which corresponds to 30 to 40 mm per plate. Thus, even a stack of 500 thin film culture plates can, in some cases, be accommodated within 15-20 cm of height.

The height of the pusher is typically less than the height of a single culture plate, such that a portion of the lower most culture plate cover slip fits over the pusher. Notably, However, it is also possible for the pusher to be about the same or even slightly higher than the height of a single culture plate; this is especially true when the cover slip is somewhat flexible, thereby permitting the cover slip to be positioned above the pusher even when the pusher is somewhat higher than the culture plate. By fitting over the pusher, the cover slip can serve to guide the pusher to push only the lowermost culture plate, for example in a stack of culture plates, and prevent the pusher from pushing the culture plates that are above the lowermost culture plate, even when the culture plates are not perfectly aligned in a stack on the base. Thus, the design of the pusher helps prevent the apparatus from pushing multiple culture plates forward at once. Notably, because the pusher is not necessarily adjacent to or resting on the base, the height of the pusher refers to the distance from the top of the pusher, specifically the top of the portion of the pusher that is adapted to contact the culture plate, and the first major surface of the base (i.e., the surface of the base on which the culture plate resides).

The upright member can be attached to the base in any convenient way. It is often convenient to attach the upright member to the base by way of legs on either side of the precision gap. These legs, which are preferably adjustable so as to allow the height of the precision gap to be altered, will be located such that the precision gap is wide enough to permit a culture plate to pass through. Alternatively, the upright member need not be attached to the base. In such cases, it is supported in some other way, for example, by being attached to a culture plate loader or culture plate dispenser that incorporates the culture plate dispenser. It is possible to configure the upright member such that its height above the first surface of the base is adjustable. In this manner, the height of the precision gap can be changed by the user depending on the type of culture plater, such as thin film culture plate, that is being used in the device.

The upright member and precision gap are also designed to prevent multiple culture plates from being dispensed at once. Even though the pusher is typically configured to push only the lowest culture plate in a stack, it is possible that other culture plates can be dragged along with the lowest culture plates because of friction or other factors that cause the plates to stick together. The precision gap can mitigate or eliminate this problem, because the precision gap is not large enough to allow more than one culture plate to pass through it.

The culture plate dispensing apparatus described herein can, in operation, prevent more than one culture plate, such as a thin film culture plate, from being dispensed at a time. This overcomes a significant problem in the art. Specifically, when culture plates, particularly thin film culture plates, are stacked in a dispensing apparatus that is designed to dispense the culture plate on the bottom of the stack, the culture plate above the one on the bottom can stick to the bottom culture plate. This can cause problems such as dispensing more than one culture plate at a time, jamming the culture plate dispenser, or even damaging the culture plate reader.

Once a culture plate is dispensed from the culture plate dispensing apparatus described herein, the culture plate can be deposited in a culture plate reader. In some cases, it is deposited directly into the culture plate reader. In other cases, the culture plate is first deposited into a culture plate loader that then loads the culture plate into a culture plate reader. The culture plate loader can include one or more rollers, at least one of which is typically mechanically driven. For example a pinch roller assembly, which includes two rollers configured to simultaneously grip the top and bottom of a dispensed culture plate, can be employed.

The culture plate dispensing apparatus, culture plate loader, and culture plate reader as described herein are often specially adapted to be compatible with thin film culture plates, and particularly with those available under the trade designation PETRIFILM plates.

Referring to the Figures, none of which are necessarily drawn to scale, FIG. 1, dispensing apparatus 100 includes base 110 on which culture plates 130, 140, and 150 are stacked. Pusher 120 extends upright towards the stack of culture plates 130, 140, and 150, which in this Figure are thin film culture plates. Pusher 120 has a height above base 110 that is no greater than the height of culture plate 130, such that pusher 120 is under cover slip 131, which extends backwards beyond the back edge of plate 130 and over pusher 120. Upright member 160 is above base 110 on the opposite side from pusher 120. A space between the upright member 160 and base 110 defines precision gap 170.

In FIG. 1, pusher 120 is shown in a retracted position, meaning that it is merely holding culture plates 130, 140, and 150 in place but is not in the process of dispensing the lowermost culture plate 130 through precision gap 170. Thus, pusher 120 can also help to retain the lowermost culture plate 130 in place prior to dispensing.

Upright member 160 is not shown as being attached to any other part of dispensing apparatus 100. However, upright member 160 can be attached to base 110 by means of legs (not shown) that are beyond the edges of the stack of culture plates 130, 140, and 150. Alternatively, when the dispensing apparatus 100 is a component of a larger machine, such as a culture plate reader (not shown) upright member 160 can be affixed to another portion of the machine (not shown).

Precision gap 170 is at least as high, and typically slightly higher, than the height of culture plate 130 (including the height of cover slip 131), but is less than twice the height of culture plate 130 such that only one culture plate at a time can pass through precision gap 170 in direction D. Similarly, precision gap 170 is at least as wide, and often somewhat wider, than the width of culture plates 130, 140, and 150.

While only three culture plates 130, 140, and 150 are shown in FIG. 1, the dispensing apparatus can be configured to accommodate a stack with many more culture plates. As discussed above, some dispensing apparatuses can accommodate 10, 25, 50, 100, 250, 400 or even 500 or more culture plates.

In use, pusher 120 moves in direction D to push lowermost culture plate 130 in direction D and through precision gap 170, thereby separating lowermost culture plate 130 from the stack of culture plates. Pusher 120 then retracts to its original location, allowing culture plate 140 to fall onto base 110. Pusher 120 is sufficiently high (measured as the height above base 110) to push lowermost culture plate 130 but not so high as to impinge on the cover slip 131 of lowermost culture plate 130, and also does not impinge upon the cover slip of next culture plate 140 when it falls onto base 110.

Pusher 120 can be permanently attached to base 110, in which case pusher 120 and base 110 move together in direction D. More commonly, pusher 120 slides along top of base 110, and can be powered by a spring or motor (not shown).

Although the Figure shows pusher 120 in contact with base 110, this need not be the case. It is also possible for a pusher 120 to be above the base 110 without contacting it. For example, the pusher 120 can be configured as rod positioned above base 110 wherein the rod is attached to a spring that moves the rod between the retracted and engaged position in a similar fashion to the ball launcher in a pinball table.

Base 110, pusher 120, and upright member 160 can be made of any suitable material. Typically, they are made of plastic, such as polyethylene or polyethylene-co-vinylacetate. However, it is also possible for one or more of these components to be made of metal, such as aluminum, or rubber, such as silicone rubber.

Figure 2:
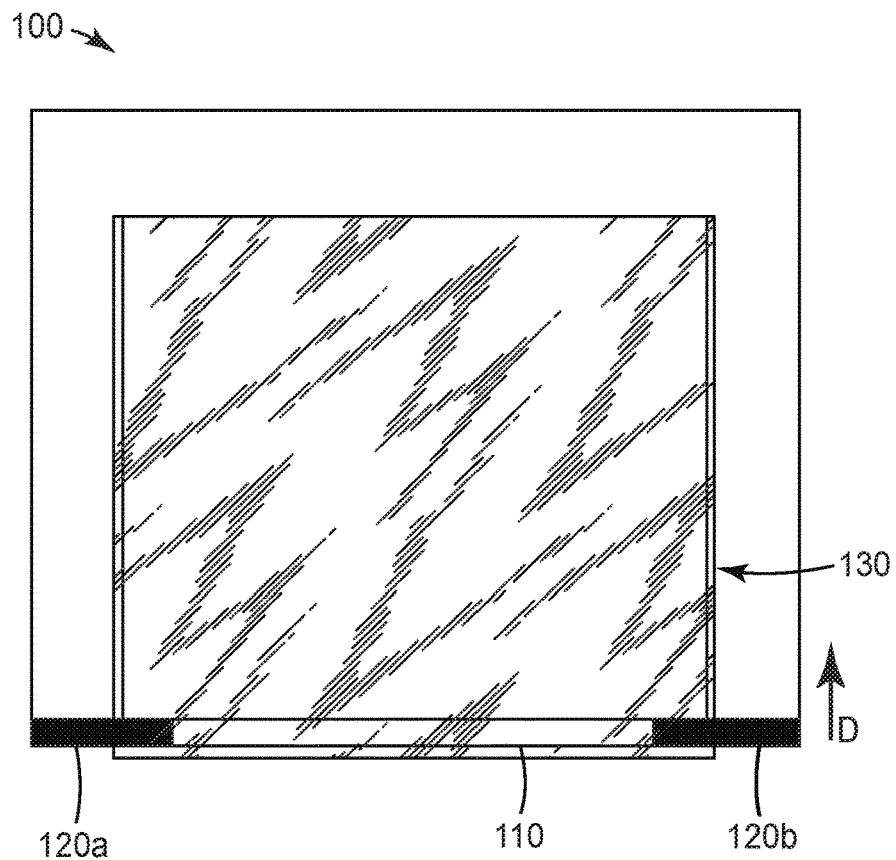
FIG. 2 is a top view of the dispensing apparatus of FIG. 1.

FIG. 2 is a top view of dispensing apparatus 100, showing base 110 with culture plate 130 resting thereon. Cover slip 131 is not shown in this view (its location, including an overhang over pusher 120, is represented by the "windowpane" hashes), which is consistent with many cover slips 131 being see-through. In this embodiment, pusher 120 is in the form of two small tabs 120a and 120b on the sides of base 100. However, it is also possible for pusher 120 to have other configurations, such as a single upright member running the length of base 110, or one or more tabs that are not adjacent to the edges of 110.

As in FIG. 1, pusher tabs 120a and 120b are retracted, meaning that they are not in the process of moving in direction D and thereby pushing culture plate 130 in direction D. In use, pusher tables 120a and 120b move in direction D in tandem to push culture plate 130 in direction D.

Figure 3:
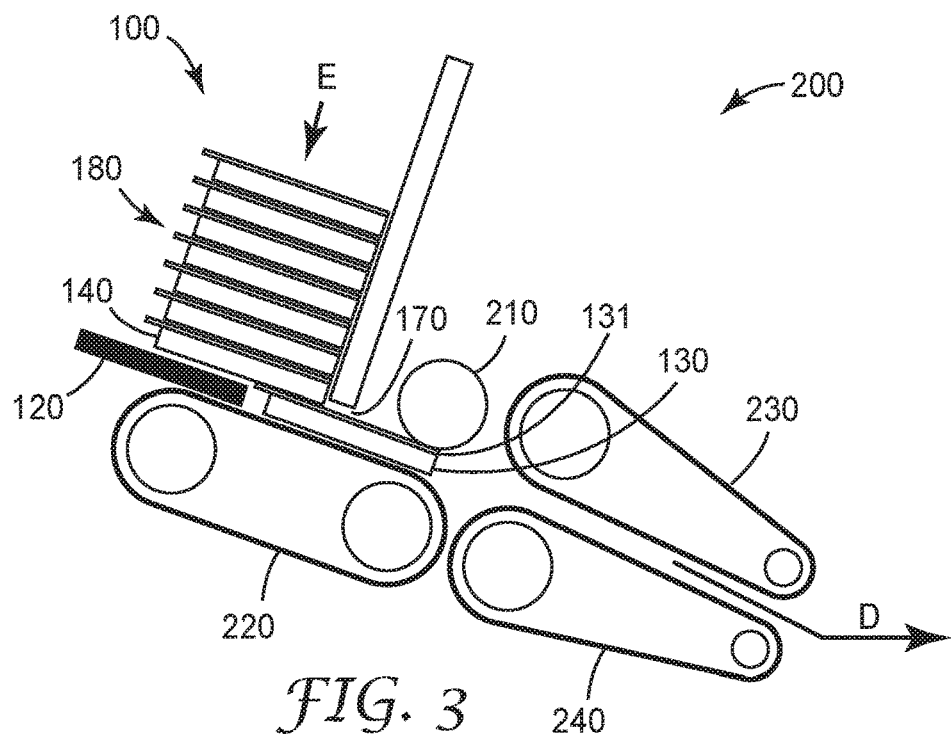
FIG. 3 is a side view of a culture plate loader featuring the dispensing apparatus of FIG. 1.

FIG. 3 a loading device 200 with dispensing apparatus 100. This figure shows pusher 120 in an engaged position and pushing lowermost culture plate 130 through precision gap 170 between upright member 160 and roller 220, which in this Figure also serves as the base, in direction D. Once part of culture plate 130 passes through precision gap 170, it can be further drawn out of the dispensing apparatus 100 by roller 210 and roller 220, one of which can be mechanically driven. Culture plate 130 can then be further transported to another location, such as a platen within a culture plate reader, by pinch rollers 230 and 240, one or both of which can be mechanically driven.

Once the lowermost culture plate 130 has completely passed through precision gap 170, pusher 120 can return to the retracted position, allowing culture plate stack 180 to drop down in direction E such that the next lowest culture plate 140 contacts base 110 and is ready to be dispensed through precision gap 170.

LIST OF ILLUSTRATIVE EMBODIMENTS

This list of embodiments is meant to aid in understanding particular aspects of the invention. It is not intended to be limiting.

1. A culture plate dispensing apparatus comprising
   a base having a first major surface, a front edge, and a back edge;
   a pusher on or above the first major surface of the base, the pusher being capable of moving from a retracted position to an engaged position, the retracted position being closer to the back edge than the engaged position;
   the pusher and base being configured such that when the pusher is in the retracted position the base is capable of supporting one or more culture plates on top of the first major surface of the base, the one or more culture plates having a back edge positionable near the pusher and a slip cover positionable over the pusher when the pusher is in a retracted position;
   an upright member positioned at least in part above a portion of the base near the front edge of the base, the space between the upright member and the base defining a precision gap large enough for a culture plate to pass through;
   wherein the precision gap is at least the height of the one or more culture plates and less than twice the height of the one or more culture plates; and
   wherein the pusher in the engaged position pushes one and only one culture plate at least partially through the precision gap.

2. The culture plate dispensing apparatus of embodiment 1, wherein the base is capable of supporting one or more culture plates in a stack having a stack height; and the upright member has a height above the first major surface of the base that is equal to or greater than the stack height.

3. The culture plate dispensing apparatus of any of the preceding embodiments,
   wherein
   each of the one or more culture plates has a height; and
      wherein the pusher has a height that is less than the height of the one or more culture plates.

4. A culture plate loader comprising the culture plate dispensing apparatus of any of the preceding embodiments; and one or more rollers positioned to move a culture plate that has passed at least partially through the precision gap away from the culture plate dispensing apparatus.

4a. The culture plate loader of embodiment 4, further comprising a pinch roller for receiving a dispensed culture plate.

5. A culture plate reader comprising a culture plate dispensing apparatus of any of embodiments 1-3 or a culture plate loader of embodiments 4 or 4a.

5a. The culture plate reader of embodiment 5, further comprising a platen for receiving a culture plate.

6. A method of dispensing a culture plate, the method comprising:
placing one or more culture plates having cover slips with an overhanging portion that overhangs at least one edge of the one or more culture plates on a base having a first major surface, a front edge, and a back edge between a pusher in a retracted position located towards the back of the base and on or above the base towards the one or more culture plates and an upright member that is positioned in part above the base and towards the front edge of the base to define a space between the upright member and the base, the space between the upright member and the base defining a precision gap, such that the overhanging portion of at least one of the cover slips is above the pusher;
engaging the pusher to move from the retracted position to an engaged position that is closer to the front edge of the base than the retracted position, thereby pushing one and only one culture plate through the precision gap.

7. The method of embodiment 6, wherein the pusher is in the form of two or more tabs.

8. The method of any of embodiments 6-7, wherein each culture plate has a height and the precision gap has a height that is greater than the height of a single culture plate but less than the height of two culture plates.

9. The method of any of embodiments 6-8, wherein the one or more culture plates comprise at least 10 culture plates; and
further wherein the overhanging portion of the cover slip of each of the at least 10 culture plates is oriented in the same direction over the pusher.

10. A method of loading a culture plate into a culture plate reader, comprising
dispensing a culture plate according to a method of any of embodiments 6-9;
moving the culture plate away from the base; and
depositing the culture plate into the culture plate reader.

11. The method of embodiment 10, wherein moving the culture plate away from the base comprises moving the culture plate along one or more rollers.

12. The method of any of embodiments 10-11 wherein depositing the culture plate into the culture plate reader comprises positioning the culture plate on a platen associated with the culture plate reader.

13. A method of counting microorganism colonies comprising loading at least one inoculated culture plate into a culture plate reader according to the method of any of embodiments 10-12 and counting at least some of the microorganism colonies on the inoculated culture plate.

14. The method of embodiment 13, wherein the culture plate is a thin film culture plate.

15. The dispensing apparatus of any of embodiments 1-5 wherein the one or more culture plates are thin film culture plates.

What is claimed is:

1. A culture plate dispensing apparatus comprising
a base having a first major surface, a front edge, and a back edge, the base comprising a roller or series of rollers;
a pusher on or above the first major surface of the base, the pusher being capable of moving from a retracted position to an engaged position, the retracted position being closer to the back edge than the engaged position;
the pusher and base being configured such that when the pusher is in the retracted position the base is capable of supporting one or more culture plates on top of the first major surface of the base, the one or more culture plates having a back edge positionable near the pusher and a slip cover positionable over the pusher when the pusher is in a retracted position;
an upright member positioned at least in part above a portion of the base near the front edge of the base to form a space between the upright member and the base, the space between the upright member and the base defining a precision gap large enough for a culture plate to pass through;
wherein the precision gap is at least the height of the one or more culture plates and less than twice the height of the one or more culture plates; and
wherein the pusher is adapted to push one and only one culture plate at least partially through the precision gap when it is moved from the retracted position to the engaged position, wherein the one or more culture plates are thin film culture plates.

2. The culture plate dispensing apparatus of claim 1, wherein the base is capable of supporting one or more culture plates in a stack having a stack height; and
the upright member has a height above the first major surface of the base that is equal to or greater than the stack height.

3. The culture plate dispensing apparatus of claim 1, wherein each of the one or more culture plates has a height; and
wherein the pusher has a height that is less than the height of the one or more culture plates.

4. The culture dispensing apparatus of claim 1, further comprising
one or more rollers positioned to move a culture plate that has passed at least partially through the precision gap away from the culture plate dispensing apparatus.

5. A culture plate reader comprising a culture plate dispensing apparatus of claim 1.

6. A method of dispensing a culture plate, the method comprising:
placing one or more thin-film culture plates having cover slips with an overhanging portion that overhangs at least one edge of the one or more culture plates on the base of the culture plate dispensing apparatus of claim 1;
engaging the pusher to move from the retracted position to an engaged position that is closer to the front edge of the base than the retracted position, thereby pushing one and only one culture plate through the precision gap.

7. The method of claim 6, wherein the pusher is in the form of two or more tabs.

8. The method of claim 6, wherein each culture plate has a height and the precision gap has a height that is greater than the height of a single culture plate but less than the height of two culture plates.

9. The method of claim 6, wherein the one or more culture plates comprise at least 10 culture plates; and
further wherein the overhanging portion of the cover slip of each of the at least 10 culture plates is oriented in the same direction over the pusher.

10. The method according to a method of claim 6 further comprising
moving the one and only one culture plate away from the base; and
depositing the one and only one culture plate into a culture plate reader.

11. The method of claim 10, wherein moving the one and only one culture plate away from the base comprises moving the one and only one culture plate along one or more rollers.

12. The method of claim 10, wherein moving and depositing the one and only one culture plate into the culture plate reader comprises positioning the one and only one culture plate on a platen associated with the culture plate reader.

13. A method of counting microorganism colonies comprising loading at least one inoculated culture plate comprising microorganism colonies into a culture plate reader according to the method of claim 10 and counting at least some of the microorganism colonies on the at least one inoculated culture plate.

14. The method of claim 13, wherein the inoculated culture plate is a thin film culture plate.

15. A culture plate reader comprising a culture plate dispensing apparatus of claim 2.

16. A culture plate reader comprising a culture plate dispensing apparatus of claim 3.

17. A culture plate reader comprising a culture plate dispensing apparatus of claim 4.

* * * * *